United States Patent [19]

Maurer

[11] Patent Number: 4,772,702

[45] Date of Patent: Sep. 20, 1988

[54] PREPARATION OF (THIONO)PHOSPHORIC ESTERS

[75] Inventor: Fritz Maurer, Wuppertal, Fed. Rep. of Germany

[73] Assignee: Bayer Aktiengesellschaft, Leverkusen, Fed. Rep. of Germany

[21] Appl. No.: 875,426

[22] Filed: Jun. 17, 1986

[30] Foreign Application Priority Data

Jul. 5, 1985 [DE] Fed. Rep. of Germany ....... 3524055

[51] Int. Cl.$^4$ ............................. C07F 9/65; C07F 9/18
[52] U.S. Cl. ................................... 544/243; 544/232;
544/337; 546/23; 546/25; 548/114; 548/116;
548/117; 548/118; 558/100
[58] Field of Search ...................... 544/243, 232, 337;
546/23, 25, 243; 548/114, 117, 116, 118;
558/100

[56] References Cited

U.S. PATENT DOCUMENTS

4,092,312 5/1978 Kroposki et al. ................... 544/243
4,357,328 11/1982 Pawloski ........................ 544/244 X

FOREIGN PATENT DOCUMENTS

0207412 1/1987 European Pat. Off. ............ 558/100

Primary Examiner—Donald G. Daus
Assistant Examiner—Diana G. Rivers
Attorney, Agent, or Firm—Sprung Horn Kramer & Woods

[57] ABSTRACT

In the preparation of a (thiono)phosphoric ester of the formula

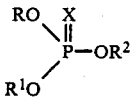

in which
X represents oxygen or sulphur,
R and $R^1$ are identical or different and represent alkyl, and
$R^2$ represents optionally substituted aryl or represents optionally substituted hetaryl having at least one nitrogen atom,
wherein a hydroxyl derivative of the formula

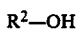

$R^2$—OH or an ammonium, alkali metal or alkaline earth metal salt thereof is reacted with a (thiono)phosphoric halide of the formula

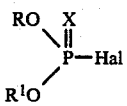

in which
Hal represents halogen,
the improvement which comprises effecting the reaction in the presence of a bicyclic organic amine as catalyst. Advantageously the reaction is effected in a diluent in the presence of potassium carbonate as an acid acceptor at 20° to 100° C., and 0.8 to 1.5 mols of the halide and 0.005 to 0.5 mol of 1,4-diazabicyacyclo-(2,2,2)-octane are used as bicyclic organic amine per mol of the hydroxyl compound.

11 Claims, No Drawings

PREPARATION OF (THIONO)PHOSPHORIC ESTERS

The invention relates to a new process for the preparation of (thiono)phosphoric esters from (thiono)phosphoric halides and hydroxyl derivatives in the presence of a bicyclic amine as catalyst.

It has already been disclosed that (thiono)phosphoric esters can be obtaiend when hydroxyl derivatives are reacted with (thiono)phosphoric halides in the presence of inorganic bases such as, for example, sodium or potassium carbonate (compare, for example, U.S. applications Ser. No. 765,908, filed Aug. 14, 1985, now pending, Ser. No. 743,456 filed June 11, 1985, now pending, DE-OS (German Published Specification) No. 3,326,510 and U.S. application Ser. No. 606,106, filed May 2, 1984, now pending.

The disadvantages of this process are that very long hold-up times are necessary, and large amounts of isomeric by-products (which are difficult to remove) are produced and this results in the yields frequently being very unsatisfactory.

It has now been found that (thiono)phosphoric esters of the formula (I)

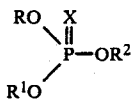

in which
X represents oxygen or sulphur,
R and $R^1$ are identical or different and represent alkyl, and
$R^2$ represent optionally substituted aryl or represents optionally substituted hetaryl having at least one nitrogen atom, are obtained when hydroxyl derivatives of the formula (II)

in which
$R^2$ has the abovementioned meaning,
or their appropriate ammonium, alkali metal or alkaline earth metal salts, are reacted with (thiono)phosphoric halides of the formula (III)

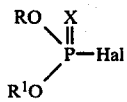

in which
X, R and $R^1$ have the abovementioned meanings, and
Hal represents halogen, in particular chlorine or bromine, in the presence of a bicyclic organic amine as catalyst, where appropriate in the presence of acid acceptors, and in the presence of a diluent, at temperatures below 0° and 120° C.

Suitable bicyclic organic amines which act as catalysts are preferably bicyclic amines having 1 or 2 bridgehead nitrogen atoms, preferably 1,4-diazabicyclo-(2,2,2)-octane (DABCO) and quinuclidine, and DABCO is particularly preferred. The bicyclic organic amine is used at least in catalytic amounts, but it may, where appropriate, also be used in molar amount to bind the hydrogen halide being produced in the reaction, if no other acid acceptor is used.

Surprisingly, it is possible by means of the process according to the invention to carry out the reaction in high yield and purity with very short hold-up times. This is all the more surprising since, according to the prior art, the formation of considerable amounts of by-products would have had to be expected.

Alkyl R and $R^1$ is straight-chain or branched alkyl preferably having 1 to 10, in particular 1 to 6, and particularly preferably, 1 to 4, carbon atoms. Examples which may be mentioned are methyl, ethyl, n-propyl, i-propyl, n-butyl, i-butyl, sec.-butyl, tert.-butyl, n-pentyl, 1-methyl-butyl, 2-methyl-butyl, 3-methyl-butyl, 1-ethyl-propyl, 2,2-dimethyl-propyl and 1,2-dimethyl-propyl. Particularly preferred alkyl radicals R and $R^1$ are ethyl and i-propyl.

Optionally substituted aryl $R^2$ is preferably phenyl or naphthyl, in particular phenyl. Aryl $R^2$ particularly preferably represents 4-nitrophenyl.

An optionally substituted heterocycle $R^2$ is a 5- or 6-member heterocycle or a bicyclic 8- to 10-member heterocycle, preferably having 2 to 9 carbon atoms and 1 to 3 nitrogen atoms and, where appropriate, one oxygen or sulphur atom.

Examples which may be mentioned are optionally substituted 1,2,4-triazol-3-yl, pyrazol-3-yl, pyrazol-4-yl, pyrazol-5-yl, imidazol-2-yl, imidazol-4-yl, oxazol-2-yl, oxazol-4-yl, oxazol-5-yl, isoxazol-3-yl, isoxazol-4-yl, isoxazol-5-yl, thiazol-2-yl, thiazol-4-yl, thiazol-5-yl, pyrid-2-yl, pyrid-3-yl, pyrid-4-yl, pyridazin-3-yl, pyrdazin-4-yl, pyrimidin-2-yl, pyrimidin-4-yl, pryimidin-5-yl.

pyrazin-2-yl, 5,6-dihydropyridazin-6-on-3-yl, 1,6-dihydro-pyrimidin-6-on-4 4-yl, benzoxazol-2-yl, benzisoxazol-3-yl, phthalazin-1-yl quinolin-2-yl, quinolin-8-yl, isoquinolin-1-yl, isoquinolin-3-yl, quinazolin-2-yl, quinazolin-4-yl and quinoxalin-2-yl. Preferred heterocyclic radicals $R^2$ are pyrimidin-2-yl, 5-bromo-pyrimidyl-2-yl, 5-tert,-butylpyrimidin-2-yl, 2-i-propyl-4-methyl-pyrimidin-6-yl and 2,3,5-trichloropyrimidin-6-yl.

The radicals which are designated as being optionally substituted can contain one or more, identical or different, substituents. Preferred substituents which may be listed are: halogen, nitro, cyano, $C_1$–$C_4$-alkyl, $C_1$–$C_4$-alkoxy, $C_1$–$C_4$-alkythio, halogeno-$C_1$–$C_4$-alkyl, halogeno-$C_1$–$C_4$-alkoxy, halogeno-$C_1$–$C_4$-alkylthio, $C_1$–$C_4$-alkylsulphinyl, $C_1$–$C_4$-alkylsulphonyl, $C_3$–$C_6$-cycloalkyl, phenyl, di-($C_1$–$C_4$)-alkylamino, $C_1$–$C_2$-alkoxy-$C_1$–$C_4$-alkyl, $C_1$–$C_2$-alkylthio-$C_1$–$C_4$-alkyl, $C_1$–$C_2$-alkylthio-$C_1$–$C_4$-alkoxy, $C_1$–$C_2$-alkylsulphinyl-$C_1$–$C_4$-alkyl, $C_1$–$C_2$-alkylsulphonyl-$C_1$–$C_4$-alkyl and/or $C_1C_4$-alkoxycarbonyl. Preferred substituents are halogen (in particular chlorine or bromine), nitro and/or $C_1$–$C_4$-alkyl.

X preferably represents sulphur.

The compounds of the formula (I) which are preferably prepared by means of the process according to the invention are those in which
X represents oxygen or sulphur (preferably sulphur),
R and $R^1$ are identical or different and represent $C_1$–$C_6$-alkyl, and
$R^2$ represents phenyl which is optionally substituted once to three times by fluorine, chlorine, bromine, nitro, cyano, $C_1$–$C_4$-alkyl, $C_1$–$C_4$-alkoxy, phenyl, $C_1$–$C_4$-alkylthio, halogeno-$C_1$–$C_4$-alkyl, halogeno-$C_1$–$C_4$-alkoxy, halogeno-$C_1$–$C_4$-alkylthio, $C_1$–$C_4$-alkylsulphinyl, $C_1$–$C_4$-alkylsulphonyl, $C_1$–$C_2$- alkylsulphinyl-$C_1$-$C_4$-alkyl, $C_1$-$C_2$-alkylsulphonyl-$C_1$-$C_4$-alkyl and/or $C_1$-$C_4$-alkoxycarbonyl; represents pyrimidin-2-yl, pryimidin-4-yl or pyrimidin-5-yl which is optionally substituted once to three times by chlorine, bromine, $C_1$-$C_4$-alkyl, $C_1$-$C_4$-alkoxy, $C_1$-$C_4$-alkylthio, $C_3$-$C_6$-cycloalkyl, phenyl, di-($C_1$-$C_4$)-alkylamino, $C_1$-$C_2$-alkoxy-$C_1$-$C_4$-alkyl, $C_1$-$C_2$-alkylthio-$C_1$-$C_1$-$C_4$-alkyl, $C_1$-$C_2$-alkylthio-$C_1$-$C_4$-alkoxy, $C_1$-$C_2$-alkylsulphinyl-$C_1$-$C_4$-alkyl and/or $C_1$-$C_2$-alkylsulphonyl-$C_1$-$C_4$-alkyl represents 1,2,4-triazol-3-yl which is optionally substituted once or twice by $C_1$-$C_4$-alkyl and/or phenyl; and represents pyrid-2-yl which is optionally substituted once to three times by chlorine, bromine and/or halogeno-$C_1$-$C_2$-alkyl.

The compounds of the formula (I) which were particularly preferably obtained according to the invention are those in which X represents oxygen or sulphur (preferably sulphur), R and $R^1$ are identical or different and represent $C_1$-$C_4$-alkyl (preferably ethyl or i-propyl), and $R^2$ represents 4-nitrophenyl, pyrimidin-2-yl, 5-bromo-pyrimidin-2-yl, 5-tert.-butyl-pyrimidin-2-yl, 2-i-propyl-4-methyl-pyrimidin-6-yl or 2,3,5-trichloropyridin-6-yl.

Halogen denotes (where nothing else is indicated) fluorine, chlorine, bromine or iodine, preferably fluorine, chlorine and bromine, in particular chlorine.

When, for example, 4-hydroxy-5-methoxy-2-methylthiomethyl-pyrimidine and O-ethyl-O-i-propyl-thionophosphoric chloride are used as starting substances in the process according to the invention, in the presence of catalytic amounts of 1,4-diazabicyclo-(2,2,2)-octaine (DABCO), then the reaction can be outlined by the diagram below:

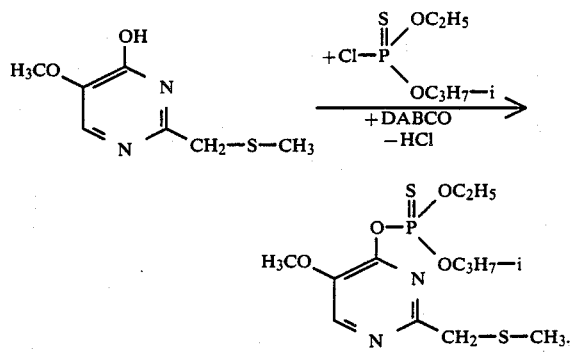

The compounds of the formula (II) are known and/or can be prepared by known methods and processes (compare, for example, U.S. application Ser. No. 68,795, filed Aug. 22, 1979, DE-OS (German Published Specification) No. 2,928,185, U.S. Pat. No. 4,503,057, U.S. Pat. No. 3,244,586, U.S. Pat. No. 4,115,540, DE-AS (German Published Specification) No. 2,260,015), DE-OS (German Published Specification) No. 2,630,054 and U.S. Pat. No. 4,152,426).

The alkali metal or alkaline earth metal salts of the compounds of the formula (II) which are preferably used are the sodium, potassium or calcium salts, and the ammonium salts which are preferably used are the ammonium or tri-$C_1$-$C_4$-alkylammonium salts, such as trimethylammonium or triethylammonium salts.

The following may be mentioned as examples of the compounds of the formula (II) or of the corresponding sodium, potassium, calcium and ammonium salts: phenol, 2-cyano-, 2-nitro-, 2-chloro-, 2-bromo-, 2-phenyl-, 2-methyl-, 2-ethyl-, 2-n-propyl-, 2-iso-propyl-, 2-n-butyl-, 2-iso-butyl-, 2-sec.-butyl-, 2-tert.-butyl-, 2-methoxy-, 2-ethoxy-, 2-n-propoxy-, 2-iso-propoxy-, 2-n-butoxy-, 2-iso-butoxy-, 2-sec.-butoxy-, 2-tert.-butyl-, 2-methylthio-, 2-ethylthio-, 2-n-propylthio-, 2-iso-propylthio-, 2-methoxycarbonyl-, 2-ethoxycarbonyl-, 2-n-propoxycarbonyl-, 2-i-propoxycarbonyl-, 3-chloro-, 3-methoxy-, 3-ethoxy-, 4-chloro-, 4-cyano-, 4-nitro-, 4-methylthio-, 4-ethylthio-, 4-methoxy-, 4-ethoxy-, 4-methylsulphonyl-, 4-ethylsulphonyl-, 4-methyl-, 4-ethyl-, 4-n-propyl-, 4-iso-propyl-, 4-n-butyl-, 4-iso-butyl-, 4-sec.-butyl-, 4-tert.-butyl-, 2,4-dichloro- and 2,4-dimethylphenol; 2-hydroxy-pyridine, 6-chloro-, 6-bromo-, 6-fluoro-, 3,4-dichloro-, 3,5-dichloro-, 3,6-dichloro-, 3,5-dibromo-, 3,4,5-trichloro-, 3,5,6-trichloro-, 4,5,6-trichloro-, 3,4,5,6-tetrachloro- and 5-trifluoromethyl-2-hydroxy-pyridine; 1-methyl-, 1-ethyl-, 1-n-propyl-, 1-i-propyl-, 1-n-butyl-, 1-i-butyl-, 1-sec.-butyl-, 1-tert.-butyl-, 1-phenyl-5-chloro- and -5-bromo-3-hydroxy-1,2,4-triazole and 3-hydroxy-1,2,4-triazole; 2-hydroxy-pyrimidine, 4-hydroxy-pyrimidine, 5-hydroxy-pyrimidine; 5-fluoro-, 5-chloro-and 5-bromo-2-hydroxy-pyrimidine; 2-isopropyl-, 6-methyl-, 2,6-dimethyl-, 2-ethyl-6-methyl-, 2-n-propyl-6-methyl-, 2-i-propyl-6-methyl-, 2-n-butyl-6-methyl-, 2-i-butyl-6-methyl-, 2-sec.-butyl-6-methyl-, 2-tert.-butyl-6-methyl-, 6-tert.-butyl-, 2-methyl-6-tert.-butyl-, 2-methoxy-6-methyl-, 2-ethoxy-6-methyl-, 2-i-propoxy-6-methyl-, 2-methylthio-6-methyl-, 2-i-propylthio-6-methyl-, 2-phenyl-6-methyl-, 2-cyclopropyl-6-methyl-, 2-cyclohexyl-6-methyl-, 2-dimethylamino-6-methyl-, 2-diethylamino-6-methyl-, 2-methoxymethyl-5-methoxy-, 2-methylthiomethyl-5-methoxy-, 2-methylsulphinylmethyl-5-methoxy-, 2-methylsulphonylmethyl-5-methoxy-, 2-methylthiomethyl-5-ethoxy-, 2-methoxymethyl-5-ethoxy-, 2-i-propyl-5-methylthio-, 2-i-propyl-5chloro-6-methyl-, 2-tert.-butyl-5-chloro-6-methyl-, 2-i-propyl-5-bromo-6-methyl-, 2-tert.-butyl-5-bromo-6-methyl-, 6-phenyl-, 2-methyl-6-phenyl-, 2-i-propyl-6-phenyl-, 2-ethyl-6-ethoxy-, 2-i-propyl-6-methoxy-, 2-i-propyl-6-ethoxy-, 2-tert.-butyl-6-methoxy-, 2-i-propyl-6-(methylthio-methoxy)-, 2-cyclopropyl-6-ethoxy- and 2-i-propyl-5,6-dimethyl-4-hydroxypyrimidine; 2-methyl-, 2-ethyl-, 2-n-propyl-, 2-i-propyl-, 2-n-butyl-, 2-i-butyl-, 2-sec.-butyl-, 2-tert.-butyl-, 2-phenyl-, 2-cyclopropyl-, 2-cyclobutyl-, 2-cyclopentyl-, 2-cyclohexyl-, 2-cyclopropyl-4-methyl-, 2-phenyl-4-methyl-, 2,4-dimethyl-, 2-ethyl-4-methyl-, 2-n-propyl-4-methyl-, 2-i-propyl-4-methyl-, 2-n-butyl-4-methyl-, 2-i-butyl-4-methyl-, 2-sec.-butyl-4-methyl-, 2-tert.-butyl-4-methyl-, 2-cyclopropyl-4-ethyl-, 2-phenyl-4-ethyl-, 2-methyl-4-ethyl-, 2,4,-diethyl-, 2-n-propyl-4-ethyl-, 2-i-propyl-4-ethyl-, 2-n-butyl-4-ethyl-, 2-i-butyl-4-ethyl-, 2-sec.-butyl-4-ethyl- and 2-tert.-butyl-4-ethyl-5-hydroxy-pyrimidine.

The compounds of the formula (III) are known.

The following may be mentioned as examples of compounds of the formula (III): O,O-dimethyl, O,O-diethyl, O-O-di-n-propyl, O,O-di-i-propyl, O,O-di-n-butyl, O,O-di-i-butyl, O-methyl O-ethyl, O-methyl O-n-propyl, O-methyl O-i-propyl, O-methyl O-i-propyl, O-methyl O-n-butyl, O-methyl O-i-butyl, O-methyl O-sec.-butyl, O-methyl O-tert.-butyl, O-ethyl O-n-propyl, O-ethyl O-i-propyl, O-ethyl O-n-butyl, O-ethyl O-i-butyl, O-ethyl O-sec.-butyl, O-ethyl O-tert.-butyl, O-n-propyl O-i-propyl, O-n-propyl )-n-butyl, O-n-propyl O-i-butyl, O-n-propyl O-sec.-butyl, O-n-propyl O-tert.-butyl, O-i-propyl O-n-butyl, O-n-butyl O-i-butyl, O-n-butyl O-sec.-butyl and O-n-butyl O-tert.-butyl phosphoric diester chloride or bromide, and the corresponding thiono analogues.

The process according to the invention for the preparation of (thiono)phosphoric esters is generally carried out using diluents. Virtually all inert organic solvents are suitable for this. These include, in particular, aliphatic and aromatic, and optionally chlorinated aliphatic or aromatic hydrocarbons, such as petroleum ether, benzene, toluene, xylene, methylene chloride, chloroform, carbon tetrachloride, chlorobenzene and o-dichlorobenzene, ethers such as diethyl and dibutyl ether, tetrahydrofuran and dioxane, ketones such as acetone, methyl ethyl, methyl isopropyl and methyl isobutyl ketone, as well as nitriles such as acetonitrile and propionitrile.

The process according to the invention is carried out in the presence of a bicyclic organic amine, preferably in the presence of 1,4-diazabicyclo-(2,2,2)-octane (DABCO) as catalyst. The bicyclic organic amine can simultaneously also be used as acid acceptor. In this case, at least molar amounts of the bicyclic organic amine are used.

If the bicyclic organic amine is not simultaneously functioning as acid-binding agent, it is carried out using acid acceptors. It is possible to use all customary acid-binding agents as acid acceptors. Alkali metal carbonates, such as sodium and potassium carbonate, have proved parrticularly suitable, as have aliphatic, aromatic or heterocyclic amines, for example triethylamine, trimethylamine, dimethylaniline, dimethylbenzylamine and pyridine.

In a preferred embodiment, alkali metal carbonates, in particular $Na_2CO_3$ and/or $K_2CO_3$, are used as acid acceptors, and catalytic amounts of DABCO are used as catalyst.

The process according to the invention is generally carried out at temperatures between 0° C. and 120° C. The temperature range between 20° C. and 100° C. is preferred. The reactions are generally carried out under atmospheric pressure.

To carry out the process according to the invention, advantageously 0.8 to 1.5, preferably 1.0 to 1.3, in particular 1.0 to 1.2, mols of (thiono) phosphoric halide of the formula (III) are used for 1 mol of hydroxyl derivative of the formula (II). Advantageously 0.005 to 0.5, preferably 0.01 to 0.08, in particular 0.02 to 0.06, mol of bicyclic organic amine (in particular DABCO) are used per mol of the hydroxyl compound of the formula (II).

The reaction is generally carried out in a diluent in the presence of an acid acceptor. The acid acceptor is added in amounts which are suitable to bind the hydrogen halide which is being produced. Preferably, 0.8 to 1.5, in particular 0.9 to 1.3, and particularly preferably 1.0 to 1.2, mols or equivalent of acid acceptor are used per mol of hydroxyl derivative of the formula (II). After the reaction is complete, the mixture is filtered and the solvent is removed by distillation in vacuo.

The compounds of the formula (I) are obtained in the forms of oils, some of which cannot be distilled without decomposition, but from which the last volatile fractions are removed, and are in this way purified, by so-called "incipient distillation", that is to say by prolonged heating under reduced pressure at moderately elevated temperatures. The refractive index is used to characterize them.

The compounds of the general formula (I) which can be obtained according to the invention are valuable pest-combating agents. They are distinguished, in particular, by an outstanding insecticidal, acaricidal and nematicidal action. They act against plant pests, pests in the hygiene sector and pests of stored products. They have a low phytotoxicity and a good action against both sucking and biting insects and mites.

For this reason, the compounds of the general formula (I) which can be obtained according to the invention can be used successfully as pest-combating agents in plane protection is well as in the hygiene, product protection and veterinary sector.

The compounds of the formula (I) which can be obtained according to the invention can be applied to the plants or soil in the customary formulations (containing 0.5 to 95% of active compound), such as dusting powders, granules, emulsifiable concentrates, wettable powders or ultralow-volume formulations, in the customary manner, where appropriate after dilution with water. Advantageously, about 0.1 to 2.5 kg of active compound are used per hectare of area to be treated.

Many of the compounds which can be obtained according to the invention, and their use, are known and are described, for example, in U.S. Pat. Nos. 4,127,652, 4,190,652, 4,127,652, DE-OS (German Published Specification) No. 3,326,510, European Patent A No. 0,009,566, U.S. Pat. Nos. 4,325,948, 4,444,764, 4,429,125, 3,244,586 and U.S. application Ser. No. 606,106, filed Aug. 2, 1984, now pending.

PREPARATION EXAMPLES

Example 1

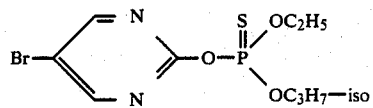

0.2 g (0.0018 mol) of diazabicyclooctane (DABCO) is added, at 20° C., to a mixture of 17.5 g (0.1 mol) of 2-hydroxy-5-bromopyrimidine (preparation U.S. Pat. No. 4,093,718), 20.7 g (0.15 mol) of potassium carbonate, 20.2 g (0.1 mol) of O-ethyl O-i-propyl thionophosphoric diester chloride and 300 ml of acetonitrile. The reaction mixture is then stirred for one hour without heating, 400 ml of toluene are added, and the mixture is shaken twice with 200 ml of water each time. The organic phase is separated off, dried over sodium sulphate and evaporated in vacuo.

After incipient distillation at 80° C. under high vacuum, 27 g (79% of theory) of O-ethyl O-i-propyl O-(5-bromopyrimidine-2-yl) thionophosphate are recovered in the form of a pale brown oil with refractive index $n_D^{22}$: 1.5179.

Example 2

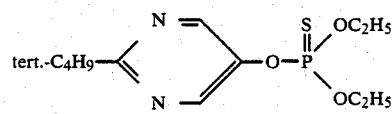

344 g (1.82 mol) of O,O-diethyl thionophosphoric diester chloride are added, in one portion, to a mixture of 277 g (1.82 mol) of 2-tert.-butyl-5-hydroxypyrimidine, 306.3 g (2.22 mol) of potassium carbonate, 12.4 g (0.11 mol) of DABCO and 2 l of toluene. This results in an increase in the temperature to about 35° C. The mixture is then stirred without heating for 4 hours, inorganic salt is filtered off with suction and washed with toluene, and the filtrate is then evaporated in vacuo. The residue is subjected to incipient distillation at 60° C. under high vacuum.

In this way 516 g (93% of theory) of O,O-diethyl O-(2-tert.-butyl-pyrimidin-5-yl) thionophosphate of refractive index $n^{26}$: 1.4902 are obtained.

In analogy to Example 1 and 2, for example the following compounds can be prepared:

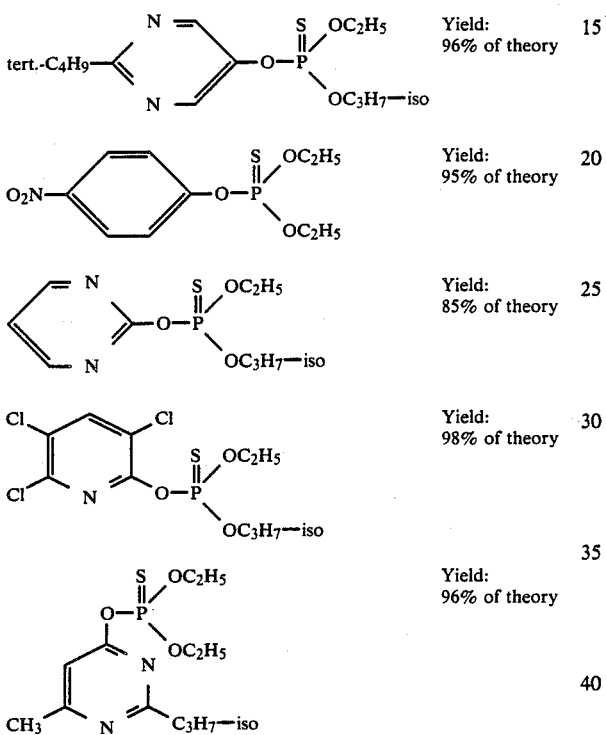

Comparison Example (without catalyst)

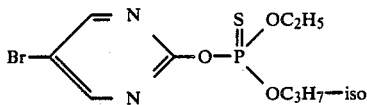

A mixture of 17.5 g (0.1 mol) of 2-hydroxy-5-bromopyrimidine (preparation DE-OS (German Published Specification) No. 2,507,702), 20.7 g (0.15 mol) of potassium carbonate, 20.2 g (0.1 mol) of O-ethyl O-i-propyl thionophosphoric diester chloride and 300 ml of acetonitrile is stirred at 50° C. for 23 hours. It is then cooled to 20° C., 400 ml of toluene are added, and the mixture is shake twice with 200 ml of water each time. The organic phase is separated off, dried over sodium sulphate and evaporated in vacuo.

After incipient distillation at 80° C. under high vacuum, 12.8 g (38% of theory) of O-ethyl O-i-propyl O-(5-bromopyriidin-2-yl) thionophosphate remain in the form of a pale brown oil of refractive index $n^{21}$: 1.5182.

It will be understood that the specification and examples are illustrative but not limitative of the present invention and that other embodiments within the spirit and scope of the invention will suggest themselves to those skilled in the art.

I claim:

1. In the preparation of a (thiono) phosphoric ester of the formula

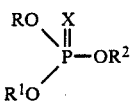

in which

X represents oxygen or sulphur,

R and $R^1$ are identical or different and represent $C_1-C_6$-alkyl, and $R^2$ represents phenyl which is optionally substituted once to three times by fluorine, chlorine, bromine, nitro, cyano, $C_1-C_4$-alkyl, $C_1-C_4$alkoxy, phenyl, $C_1-C_4$-alkylthio, halogeno-$C_1-C_4$ alkyl, halogeno-$C_1-C_4$-alkoxy, halogeno-$C_1-C_4$ alkylthio, $C_1-C_4$-alkylsulphinyl, $C_1-C_4$-alkylsulphonyl, $C_1-C_2$-alkylsulphinyl-$C_1-C_4$-alkyl, $C_1-C_2$-alkylsulphonyl-$C_1-C_4$-alkyl and/or $C_1-C_4$-alkoxycarbonyl; represents pyrimidin-2-yl, pyrimidin-4-yl or pyrimidin-5-yl which is optionally substituted once to three times by chlorine, bromine, $C_1-C_4$-alkyl, $C_1-C_4$-alkoxy, $C_1-C_4$-alkylthio, $C_3-C_6$-cycloalkyl, phenyl, di-($C_1-C_4$)-alkylamino, $C_1-C_2$-alkoxy-$C_1-C_4$-alkyl, $C_1-C_2$-alkylthio-$C_1-C_4$-alkyl, $C_1-C_2$-alkylthio-$C_1-C_4$-alkoxy, $C_1-C_2$-alkylsulphinyl-$C_1-C_4$-alkyl and/or $C_1-C_2$-alkylsulphonyl-$C_1-C_4$-alkyl; or represents pyrid-2-yl which is optionally substituted once to three times by chlorine, bromine and/or halogeno-$C_1-C_2$-alkyl, wherein a hydroxyl derivative of the formula $R^2$—OH or an ammonium, alkali metal or alkaline earth metal salt thereof is reacted with a (thiono)phosphoric halide of the formula

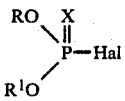

in which

Hal represents halogen, the improvement which comprises affecting the reaction in a single phase in the presence of 1,4-diazabicyclo-(2,2,2)-octane (DABCO) as the sole amine catalyst.

2. A process according to claim 1, in which

R and $R^1$ are identical or different and represent $C_1-C_4$-alkyl and $R^2$ represents 4-nitrophenyl, pyrimidin-2-yl, 5-bromopyrimidyl-2-yl, 5-tert.-butyl-pyrimidin-2-yl, 2-i-propyl-4-methyl-pyrimidin-6-yl or 2,3,5-trichloropyridin-6-yl, and Hal represents chlorine.

3. A process according to claim 1, in which

X represent sulphur.

4. A process according to claim 1, in which

X represents sulphur,

R represents ethyl, $R^1$ represents i-propyl, $R^2$ represents 5-tert.-butyl-pyrimidin-2-yl, and Hal represents chlorine.

5. A process according to claim 1, wherein the reaction is carried out at 0° to 120° C.

6. A process according to claim 1, wherein the reaction is carried out at 20° to 100° C.

7. A process according to claim 1, wherein 0.8 to 1.5 mols of the halide are used per mol of the hydroxyl compound.

8. A process according to claim 1, wherein 0.005 to 0.5 mol of 1,4-diazabicyclo-(2,2,2)-octane is used as catalyst per mol of the hydroxyl compound.

9. A process according to claim 1, wherein the reaction is effected in the presence of potassium carbonate as an acid acceptor.

10. A process according to claim 1, wherein the reaction is effected in a diluent.

11. A process according to claim 4, wherein the reaction is affected in a diluent in the presence of potassium carbonate as an acid acceptor at 20° to 100° C., and 0.8 to 1.5 mols of the halide and 0.005 to 0.5 mol of 1,4-diazabicyclo-(2,2,2)-octane are used per mol of the hydroxyl compound.

* * * * *